(12) United States Patent
Ruban et al.

(10) Patent No.: US 8,209,902 B2
(45) Date of Patent: Jul. 3, 2012

(54) BIOLOGICALLY ACTIVE MULTIFUNCTIONAL NANOCHIPS AND METHOD OF APPLICATION THEREOF FOR PRODUCTION OF HIGH-QUALITY SEED

(75) Inventors: Igor Nikolaevich Ruban, Tashkent (UZ); Nadejda Leonidovna Voropaeva, Tashkent (UZ); Oleg Lvovich Figovsky, Haifa (IL); Muzaffar Dzhahangulovich Sharipov, Tashkent (UZ); Talaat Karimovich Dadajanov, Tuzel (UZ)

(73) Assignees: Nanotech Industries, Inc., Daly City, CA (US); Polymate, Ltd., Migdal Ha'emeq (IL)

( * ) Notice: Subject to any disclaimer, the term of this patent is extended or adjusted under 35 U.S.C. 154(b) by 562 days.

(21) Appl. No.: 12/459,518

(22) Filed: Jul. 2, 2009

(65) Prior Publication Data
US 2011/0000411 A1    Jan. 6, 2011

(51) Int. Cl.
*A01C 1/06*   (2006.01)
(52) U.S. Cl. .......................................................... 47/57.6
(58) Field of Classification Search .................... 47/57.6
See application file for complete search history.

(56) References Cited

U.S. PATENT DOCUMENTS

| | | | | |
|---|---|---|---|---|
| 2,579,734 A | * | 12/1951 | Burgesser | 47/57.6 |
| 3,947,996 A | * | 4/1976 | Watts | 47/57.6 |
| 3,950,891 A | * | 4/1976 | Hinkes | 47/57.6 |
| 4,245,434 A | * | 1/1981 | Green | 47/80 |
| 6,202,346 B1 | * | 3/2001 | Lyons et al. | 47/57.6 |
| 6,228,883 B1 | | 5/2001 | Riggs | |
| 6,730,312 B2 | | 5/2004 | Schneidersmann et al. | |
| 6,903,093 B2 | | 6/2005 | Asrar et al. | |
| 7,081,436 B2 | | 7/2006 | Sun | |
| 7,307,043 B2 | | 12/2007 | Schlatter et al. | |
| 2004/0063582 A1 | | 4/2004 | Johnson | |
| 2009/0265980 A1 | * | 10/2009 | Spittle et al. | 47/9 |
| 2011/0000411 A1 | * | 1/2011 | Ruban et al. | 111/200 |
| 2011/0059529 A1 | * | 3/2011 | Wilson | 435/421 |

* cited by examiner

*Primary Examiner* — Frank T Palo
(74) *Attorney, Agent, or Firm* — Haynes and Boone, LLP; Pavel I. Pogodin

(57) ABSTRACT

Proposed is a biologically active nanochip for treating seeds of agricultural plants in order to improve seed germination conditions and development of plants and for protecting plants from anticipated and averaged adverse conditions. The biologically active nanochip contains a solid porous carrier, such as mineral, clay, turf, or polymer, the pores of which are intended for accommodating nanoparticles of biologically active substances that penetrate the pores when the substances are applied onto the nanochip surface, e.g., by spraying. Alternatively, the biologically active substances can be retained on the surface of the carrier by adhesion. The composition of the biologically active nanochips is selected with reference to anticipated and averaged adverse conditions. Also proposed is a method for application of the biologically active substances onto the surfaces of the biologically active nanochips.

20 Claims, No Drawings

BIOLOGICALLY ACTIVE MULTIFUNCTIONAL NANOCHIPS AND METHOD OF APPLICATION THEREOF FOR PRODUCTION OF HIGH-QUALITY SEED

FIELDS OF THE ART

The present invention relates to the field of agriculture and, more specifically, to nanotechnology in preparation of seed for sowing, in particular, to biologically active multifunctional nanochips and to the method of application for production of high-quality seed.

BACKGROUND OF THE INVENTION

Contemporary agricultural production is conducted while being exposed to global natural and anthropogenic challenges. Climate changes, environmental pollution with ecotoxicants, emergence of large arid areas, substrate salinization, and water shortage result in a reduction in the agricultural planting footprint, lower plant tolerance to adverse environmental factors, and the emergence of new populations of pathogenic microorganisms and cultural plant pests along with their rising aggressiveness. All of the above factors result in decreased agricultural yields, lower-quality produce, seed with short shelf life and low germination, and price increases in consumer markets.

To improve adaptability of plants to adverse factors in storage, to obtain full-value and healthy sprouts and good plant development, and to increase seed productivity and quality in subsequent generations, a new agrobiological nanotechnology has been developed that features a composition with properties, such as lability and mobility, that can be modified based on predictions to ensure steady seed production and plant growth and to improve the agricultural industry in general.

Heretofore, methods and compositions have been known in the art for treating seeds to improve productivity of high crops, tolerance to changes in weather conditions, resistance to pathogenic microorganisms and cultural plant pests, etc.

For example, U.S. Pat. No. 6,228,883 issued on May 8, 2001 to J. Riggs discloses a method for combating plant fungi, which consists of applying to the seeds or tubers of the plant a fungicidal composition comprising a fungicidally effective amount of a 2-alkoxyiminoacetamide compound, optionally in admixture with one or both of an alkylene bis-dithiocarbamate complex salt and a thiophanate compound. Also described are compositions comprising a fungicidally effective amount of a 2-alkoxyiminoacetamide compound, an alkylene bis-dithiocarbamate complex salt, and a thiophanate compound.

U.S. Pat. No. 6,730,312 issued on May 4, 2004 to F. Schneidersmann, et al, provides a quaternary composition for controlling microorganisms and insects or representatives of the order Acarina. The composition comprises (A) an insecticidally effective amount of at least one neonicotinoid or phenylpyrazole insecticide, and (B) a fungicidally effective amount of at least three fungicides including (B1) at least one phenylamide (acylalanine type), (B2) at least one phenylpyrrole, and (B3) at least one triazole.

U.S. Patent Application Publication No. 20040063582 published on Apr. 1, 2004 (W. Johnson, inventor) discloses a seed treatment composition containing plant macronutrients, micronutrients, a pest inhibitor, and at least one growth regulator. The composition additionally contains a vitamin component, an amino acid component, a penetrant, and an energy source. The treatment material contains macronutrients, micronutrients, vitamins, humic acid, a pest inhibitor, a mold inhibitor, an absorbant, a penetrant and growth regulators. A method of forming the composition consists of forming the initial mixture comprising water, micronutrients, and a chelating agent. The initial mixture is then converted into a second mixture by adding starch, phosphate, potassium, seaweed extract, ammonium sulfate, magnesium sulfate, a vitamin/cofactor component, and a penetrant. The chelating agent comprises humic acid.

U.S. Pat. No. 6,903,093 issued on Jun. 7, 2005 to J. Asrar, et al, discloses a method of preventing damage to the seed, shoot, and foliage of a plant by a pest. The method comprises treating the seed from which the plant grows with a composition that includes a combination of thiamethoxam and at least one pyrethrin or synthetic pyrethroid which is selected from the group consisting of taufluvalinate, flumethrin, trans-cyfluthrin, kadethrin, bioresmethrin, tetramethrin, phenothrin, empenthrin, cyphenothrin, prallethrin, imiprothrin, allethrin, and bioallethrin. The treatment is applied to the unsown seed. In another embodiment, the seed is a transgenic seed having at least one heterologous gene encoding for the expression of a protein having pesticidal activity against a first pest, and the composition has activity against at least a second pest. Treated seeds are also provided.

U.S. Pat. No. 7,081,436 issued on Jul. 25, 2006 to J. Sun discloses a composition comprising a seed treatment formulation and an organosilicone additive of the formula:

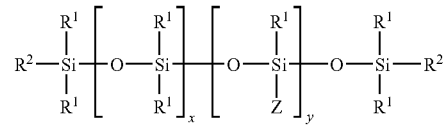

wherein X is a number from 0 to 30; Y is a number from 0 to 10; each R1 and R2 is independently selected from the group consisting of alkyl moieties from 1 to 18 carbon atoms, provided that if Y is 0, at least one R2 is Z; Z is R3OBnG; R3 is an alkylene moiety from 1 to 4 carbon atoms; B is an alkylene oxide moiety selected from the group consisting of ethylene oxide, propylene oxide, butylene oxide, and mixtures thereof; n is a number from 1 to 50 if and only if B contains ethylene oxide; otherwise, n is a number from 1 to 10; and G is selected from the group consisting of hydrogen, hydrocarbon moieties from 1 to 18 carbon atoms, and acetyl.

U.S. Pat. No. 7,307,043 issued on Dec. 11, 2007 to C. Schlatter, et al, discloses an aqueous composition suitable for applying insecticides or acaricides to plant propagation materials comprising water, an insecticidally or acaricidally effective amount of at least one nitroimino- or nitroguanidino-compound in free form or in an agrochemically useful salt form and a blend of the following components by weight: a) 2 to 10% of a surface-active agent comprising at least one anionic surfactant; b) 4 to 20% of at least one inorganic solid carrier; and c) 3 to 25% of at least one antifreeze agent. In one embodiment, the aqueous composition further comprises a fungicidally effective amount of at least one fungicidally active compound.

However, the compositions and methods described above are insufficient when considering harshly changing environmental exposures and the fact that subsequent seed generations do not always meet the required planting seed preservation criteria and demonstrate poor field-germination performance.

OBJECTS AND SUMMARY OF THE INVENTION

It is an object of the invention to provide physiologically active multifunctional nanochips and a method of application for production of high-quality seed. It is another object to provide the aforementioned nanochips to be pretreated for sowing on the basis of a nanotechnology that enhances seed and plant adaptability to real-life adverse environmental conditions and to be constructed as multifunctional nanochips that are integrated in the nanopores of the seed cover. It is a further object to provide a method for presowing treatment wherein based on a prediction of adverse effects on plant growing, the composition and properties of the biologically active nanochips can be modified by populating pores of carriers with appropriate biologically active nanoparticles and phytosanitary nanoparticles, which enhance plant tolerance to new adverse environmental factors, improve germination properties, and increase yield and productivity. Further objects are to provide the aforementioned chips and method of application that will:

extend seed dormancy, allow the planting seeds to be stored for a long time without compromising quality, initialize termination of seed dormancy under changing environmental conditions by using variously composed and structured biologically active nanochips for seed preparation before planting, enhance seed germination, enhance seed tolerance to pathogens, salinization, draught, frost, and other adverse environmental effects, increase yield, improve produce quality, reduce the rate of consumption of physiologically active and phytosanitary components, and easily adapt to currently existing technologies of seed preparation for planting.

The biologically active nanochip of the invention comprises a carrier (such as mineral, clay, turf, or polymer) having nanopore-filling molecules of physiologically active substances (such as plant development and growth control components, micro- and macro-elements of plant nutrition, phytosanitary substances, etc.). Depending on the nature and structure of the carrier, dimensions of biologically active nanochips range from several microns to 1 to 2 mm, whereas pores of the carrier may range from less than 2 nm (micropores) to 2 to 50 nm (mesopores), or 50 nm and greater (macropores). Herein, the prefix "nano" is used in view of nano dimensions of the carrier pores.

The biologically active nanochip of the invention contains biologically active components that protect the plants from unfavorable factors and increase production efficiency of agricultural goods. Each biologically active nanochip has a carrier with nanopores penetrable by the aforementioned biologically active substances. When, after sowing, the seeds come into contact with moisture, the physiologically active substances that fill the pores of the carrier are "sucked" through the pores of the seeds into a space between the seed coat and seed embryo where they fulfill their functions. According to another aspect of the invention, the carrier, which is preloaded with respective physiologically active and phytosanitary substances, is ground to the dimension of the carrier pores, and then the finely ground carriers with physiologically active components are incorporated into the nanopores of the seed cover by means of any conventional method of presowing treatment of seeds (wetting, spraying, blowing, powdering, encapsulating, incrusting, etc.). The method and biologically active nanochips of the invention apply to seed of various types, such as cotton seed, sugar-beet seed, rice seed, etc.

DETAILED DESCRIPTION OF THE INVENTION

The invention relates to natural nano devices, such as seeds of various plants irrespective of species, varieties, and geographical spread.

The term "nanotechnology," as used in the present patent application, covers nanoparticle-control technology that is used as a basis for developing new methods for processing, producing, and modifying states and properties of raw materials, materials, or semiproducts. "Nanotechnology" was previously known as "supramolecular architecture" and later as control of "ultradispersive particles" or "nanoparticles." In the field of biotechnology, manipulations with DNA, in view of DNA dimensions, were also referred to as "nanotechnology."

Given the fact that seeds are now produced under harshly changing environmental exposures, with the prevalence of negative exposures, subsequent seed generations do not always meet the required planting seed preservation criteria and demonstrate poor field germination performance. Other conditions adverse for normal seed germination and development of agricultural plants comprise diseases of agricultural plants, attacks from various insects, violation of balance between useful and "harmful" microflora and insects, as well as variations in environmental temperature and humidity that often do not coincide with optimal environmental conditions, which in turn weaken early development of plants. Since it is impossible to predict or forecast all such unfavorable conditions with high accuracy for massive growing of agricultural plants in actual field conditions rather than in laboratories, nanochip compositions disclosed herein and in the attached claims are designed for anticipated and averaged adverse conditions. The nanochip compositions presented herein are based on the applicants' experiences and are most optimal for treating seeds of specific agricultural plants mentioned in the examples and claims and for growing plants under anticipated and averaged adverse conditions.

In order to improve performance and enhance yield and quality, seeds should be additionally provided with physiologically active compounds and phytosanitary substances that improve seed tolerance to adverse exposures.

Phytosanitary substances comprise insectofungicides, bactericides, herbicides, nematocides, acaricides, antiviral preparations and substances that induce protective functions in plants, immunomodulators, elicitors, desiccants, etc. Phytosanitary measures are aimed at revealing and eliminating contamination of soil with weeds, as well as treating the soil affected by "diseases" and pests.

Nanotechnology development, which allows use of natural seed adaptation systems and biologically active nanochips in seed cover pores, is the most effective way to enhance seed reliability and resistance to adverse environmental factors.

Nanotechnology of the above-described type allows for modifying the composition of physiologically active substances, including phytosanitary substances, and altering their character based on specifics of nanosystem formation and on interactions of components (nanoparticles) on molecular and supramolecular levels within biologically active nanochips, depending on specific soil/climatic conditions of cultivation of various plants, specifics of diseases caused by microorganisms and soil-based and other pests, and extending planting seed shelf life without compromising planting properties.

In the context of the present patent application, the term "biologically active nanochip" designates a system that comprises a carrier (such as mineral, clay, turf, or polymer) having nanopore-filling molecules of physiologically active substances (such as plant development and growth-control components, micro- and macro-elements of plant nutrition, phytosanitary substances, etc.).

Depending on the nature and structure of the carrier, the dimensions of biologically active nanochips range from several microns to 1 to 2 mm, while pores of the carrier range from less than 2 nm (micropores) to 2 to 50 nm (mesopores), or 50 nm and greater (macropores). Herein, the prefix "nano" is used in view of nano dimensions of carrier pores.

According to one or more aspects of the invention, biologically active nanochips are applied to the surface of a seed and adhere to it, thus forming a film for protection of the seed from unfavorable environmental conditions. When, after sowing, the seed comes into contact with moisture, the physiologically active substances that fill the pores of the carrier are "sucked" through the pores of the seed into a space between the seed coat and seed embryo where they then fulfill their functions.

According to one or more aspects of the invention, the carrier, which is preloaded with respective physiologically active and phytosanitary substances, is ground to the dimension of the carrier pores, and then the finely ground carriers with physiologically active components are incorporated into the nanopores of the seed cover by means of any conventional method of presowing treatment (wetting, spraying, blowing, powdering, encapsulating, incrusting, etc.).

As mentioned above, biologically active nanochips are based on the use of carriers such as minerals, clay, peat, soot, products of modification thereof, and other systems that additionally contain stabilizers, ionogenic and nonionogenic surfactants, emulsifiers, various natural and synthetic oligomers and polymers, homopolymers and copolymers and their derivatives, as well as mixtures thereof in various proportions. In addition, biologically active nanochips incorporate molecules of physiologically active substances and phytosanitary substances, which ensure preservation of the planting seeds and their properties for a long time, seed and plant resistance to pathogens, tolerance to salinization and other adverse environmental factors, activation of growth processes, immunity enhancement, yield increase, and improved quality of produce.

The biologically active nanochips are constructed according to several methods (synthesis and modification) based on the following:

character of nanochip components, functional tasks of the chip, such as shelf life, seed and plant protection against phytopathogens and pests, enhanced tolerance to adverse environmental effects (plant salinity and draught, and the like), enhancement of growth processes, and the like, production of subsequent seed generations that have high planting properties, increased yield, and conditions under which seeds are produced and used.

According to one or more aspects of the invention, the biologically active nanochips may include ions of zinc, copper, cobalt, iron, lithium, manganese, molybdenum, and other trace elements, which function as enzyme activators and cofactors. A shortage of these substances may result in plant metabolism disorders, lower yields, and impaired quality of produce. The above list of elements does not rule out the use of other plant nutrient microelements and mesoelements.

Depending on the level of certain microelements and mesoelements in the soil and on the physiological response of certain plants to the effect of such nutrient elements, the biologically active nanochips will include various quantities and combinations of meso- and microfertilizers.

According to one or more aspects of the invention, the biologically active nanochips may also contain nutrient trace elements such as nitrogen, phosphorus, potassium and other fertilizers in the form of various salts (mono-, di-, and triphosphates, and the like) and bioorganic compounds that contribute to intensification of all vital processes that occur in a vegetable organism and constitute the basis of its functioning, growth, development, and productivity when used in various combinations and proportions based on their level of nitrogen, phosphorus, and potassium forms that are available for the plants in the soil and on plant demand for such nutrients. They can be used individually or in combination with various nutrient micro- and meso-elements. The above does not rule out the use of various sources of amino acids, proteins (casein, sericin and the like), biological humus, and other nutrients.

According to one or more aspects of the invention, the biologically active nanochips may also contain organic acids, which constitute a substrate for respiratory metabolism, as well as endogenous and exogenous plant-growth regulators (both low- and high-molecular) such as auxins, gibberellins, cytotoxins and their derivatives, as well as certain metabolites (maleic acid hydrazide) and other substances that are capable of controlling both individual metabolic elements and metabolism in general, which, depending on the seed type, plant cultivation conditions, and the need to accelerate or decelerate growth processes, will be used in various concentrations and combinations. This does not rule out the use of other regulators of plant growth and development in various quantities and proportions to enhance the planting properties of seed, to improve germination capacity, and to increase plant yield. The above does not rule out the use of micro- and meso-fertilizers, as well as various physiologically active substances in various combinations and quantities.

According to one or more aspects of the invention, the biologically active nanochips contain immunity enhancers such as natural phytoalexins and their derivatives, as well as elicitor molecules (oligo)aminopolysaccharides (chitooligosaccharides) and other substances, which will be used in various combinations to contribute to improvement of plant protective functions. This does not rule out the use of vitamins, adaptogenes, antibiotics, and other substances that improve plant immunity, resistance to viral diseases and other stress factors, and also the use of microorganisms that produce antibiotics and enzymes; the use of phenolic compounds, nitrogen fixators and other rhizospheric microorganisms, which are adaptable to higher levels of salts, ecotoxicants, and other agents that enhance plant tolerance to pathogens, contribute to providing an extended period before pathogenic microorganisms become resistant, and supply the plants with accessible and readily digestible forms of fertilizers ensuring remediation (restoration) of soil. The above does not rule out the use of antagonist microorganisms and the introduction of various active (nonimmobilized) strains and their enzymes, both individually and in combinations in various proportions and concentrations, and also immobilized agents on various carriers. The above does not rule out the combined use of biologically active substances and phytosanitary plant-protection agents in various ratios, concentrations, and combinations.

The biologically active nanochips may contain fungal disease inhibitors, microorganisms that are antagonists of plant pathogens, fungicides such as cyprocanazole, propiconazole, triadiaphenone, bromiconozol, tebuconazole, triforin, thiophante-methyl, sulfur, and other phytosanitary agents in various combinations and concentrations depending on pathogens, morbidity rate, plant cultivation conditions, and plant varieties. The above does not rule out the use of other topical and systemic fungicides that have been developed by various manufacturers and that are used for treating seeds of various plants within the framework of comprehensive plant protection actions aimed at protecting plants against fungal diseases in combination with other physiologically active agents and phytosanitary agents.

According to one or more aspects of the invention, the biologically active nanochips may also contain inhibitors of bacterial diseases or bactericides such as bronotak, bronopol, vitawax, carboxin, thyram, 2-(thiocyanomethylo)benzothiazole, dimethylol carbamide, propamocarb hydrochloride, and other agents, which, depending on pathogen species, degree of seed contamination, plant cultivation conditions, and plant species and variety, will be used in various quantities and different ratios to each other. The above does not rule out the use of other bactericidal agents, both individually and in combinations with other plant protection agents, plant growth regulators, fertilizers and other physiologically active compounds in various concentrations and proportions.

The biologically active nanochips may also contain agents for controlling various pests such as insecticides, including thiamethoxam, acephate, imidachloprid and other agents, as well as nematocides such as oxamyl, chitosan and other preparations that are used to control pests such as insects, nematodes and other pests in various quantities and combinations, depending on species of pests and plants that are being attacked. The above does not rule out the individual use of other insecticides as well as their combinations with each other and with plant-growth regulators, nutrient micro-, meso-, and macroelements, fungicides, herbicides, and other physiologically active compounds.

The biologically active nanochips may also contain herbicides or weed-control agents such as fluortamon, bispiribac sodium, tribenuron-methyl, dicamba, chlorosulfuron, prometrin, fluazifop-methyl, haloaxyfop-R-methyl, glyphosate, azimesulfuron, flumetsulam, florosulam, bensulfuron-methyl, rimsulfuron and other agents, which are used in various quantities and combinations, depending on species of weed and of the basic plant whose seeds are subjected to the preparation before sowing. The above does not rule out the individual use of future herbicides, which will be synthesized by manufacturers in mixtures with each other in various proportions and concentrations as well as their combined use with plant-growth regulators, nutrient micro-, meso-, and macroelements, insecticides and fungicides, bactericides, immunoregulators, and other physiologically active substances and phytosanitary compounds.

Carriers for physiologically active agents and phytosanitary agents that are used in the biologically active nanochips may also contain various natural sorbents and their modified forms such as natural minerals, lignin, peat, soot, cyclone fluff, clays, organoclays, schistose silicates, and other substances such as montmorillonite, hectorite, vermiculite, kaolin, saponite and the like, products of modification thereof, and other systems. The above does not rule out the use of other matrices that are capable of retaining nanoparticles of biologically active agents and phytosanitary agents on a surface or within pores.

Nanochip stabilizers are represented by various low- and high-molecular ionogenic and nonionogenic surfactants, various natural and synthetic oligomers and polymers, their homo- and copolymers (both ionogenic and nonionogenic) including vinyl-series polymers such as poly(vinyl lactams), polyvinyl acetates and the like, polyacrylonitrile, polyacrylic acid, urea formaldehyde resin and the like, oligo- and polysaccharides (pectins, starch and its copolymers, carboxymethyl cellulose and the like), amino polysaccharides (chitosan and others), products of modification thereof as well as their derivatives; proteins, lipids, mixtures of the above-mentioned substances in different ratios, concentrations and combinations, and the like. The above does not rule out the use of newly synthesized low- and high-molecular substances, which exhibit surfactant properties and which are capable of stabilizing nanoparticles and supporting their functionality. In addition, polymeric materials form a matrix that fixates multifunctional physiologically active and phytosanitary nanoclusters and nanochips.

Examples of solvents to be used for biologically active nanochip components include water, various acids, organic solvents, and other substances and multiple-component compositions, which will be used in different ratios and combinations. The above does not rule out the use of other solvents for newly synthesized oligomers and polymers, physiologically active agents and phytosanitary agents, and other components of biologically active nanochips. The pH values of the systems to be used should range from 5.0 to 8.0, and the use of the above-described systems should be specified, based on the acid/alkali balance of the soil in which the plants are cultivated. The above requirements require use of additional agents or replacement of certain components and solvents to produce optimum pH values without compromising the efficiency of the biologically active nanochips.

The composition and quantity of the biologically active nanochips to be applied to the seeds depend on the results of the monitoring of agricultural plant cultivation conditions, environmental statistics, and also predictions of the following indicators for the coming year: soil and ambient temperatures, humidity, attacks of pathogenic microorganisms, nature of diseases, seed types, true or light dormancy, as well as seed size and seed potentials such as germination energy and germinating capacity. In addition, the biologically active nanochip composition is defined with consideration of availability of digestible forms of potassium, phosphorus, nitrogen, and various nutrient trace elements such as zinc, copper, cobalt, iron, lithium, manganese, molybdenum, and other nutrient micro- and meso-elements in the soil. For this reason, nanochip components vary within the very broad range of $1 \cdot 10^{-10}\%$ to 100%. Trace quantities of nanochip components are used for steeping plant seeds, macro quantities are used for dusting seeds, and intermediate quantities are used for pelleting.

From the processing point of view, the difference in the use of biologically active nanochips for treating plant seeds having different dormancy types consists of the fact that seeds with light dormancy are treated without using additional steps, whereas seeds that have true dormancy are subjected to scarification, i.e., mechanical damage to seed cover. Scarification allows the biologically active nanochips to penetrate deep into the seed cover pores so as to affect growth activation and to contribute to and induce the protective response of the plant to phytopathogens that cause diseases, as well as to stress conditions caused by soil salinization, ecotoxicants, and shortage of molecules providing nutrition for the plants at the earliest stages of development (nutrient macro-, meso-, and microelements).

The biologically active nanochips comprise all necessary components for seed germination and for seed protection against anticipated factors adverse to seed germination and plant growth. The components are used optionally in various combinations, with at least one carrier and at least one physiologically active component being indispensable, and the components are used in the proportions (% by mass) shown below and comprising the following:

physiologically active substance(s): $1 \cdot 10^{-10}$% to 100%
carrier for physiologically active substance(s): $1 \cdot 10^{-2}$% to 10%
plant growth regulator(s): $1 \cdot 10^{-10}$% to 1%
phytosanitary agent(s): $1 \cdot 10^{-5}$% to 10%
nutrient element: $1 \cdot 10^{-2}$% to 90%
solvent: the balance.

It follows from the above that a biologically active nanochip in its simplest form comprises only two components, i.e., at least one carrier and at least one biologically active substance, both selected with reference to anticipated adverse factors such as cold weather, salinization of soil, and emergence of new populations of pathogenic microorganisms and cultural plant pests along with their rising aggressiveness, etc. The biologically active nanochips may be produced either as vendible products as agents, as dry or liquid substances, or in the form of a preparation.

The following nonlimiting examples demonstrate practical preparation of biologically active nanochips for seed germination. In these examples, the biologically active nanochip compositions vary, depending on type of culture to be grown and anticipated and averaged adverse conditions that will affect the germination capacity and growth of the plant. Since it is impossible to precisely forecast all specific external factors that may simultaneously affect seed germination and plant growth, as well as all attacks from the side of the pathogens along with variations in environmental parameters that may be closely associated with activation or suppression of pathogenic activity, the examples that follows disclose biologically active nanochips maximally filled with substances that cover a wide range of different biological activities for specific agricultural plants.

EXAMPLE 1

Composition of Biologically Active Nanochip for Rice Seed Preparation for Planting Rice seeds (see Tables 1 and 2) precalibrated and presorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 20 mL of solution per 1 kg of seeds) for 2 to 3 sec. The nanochip compositions were prepared in five different variants shown in Table 1.

To for and fix the biologically active nanochips on the surfaces of the seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

Here and hereinafter, the term "control" means untreated seeds, i.e., seeds that have not been pre-treated with biologically active nanochips of the invention.

TABLE 1

Concentration of Nanochip Components and Composition for Presowing Processing of Rice Seed

| Component | | 1 | 2 | 3 | 4 | 5 | Control |
|---|---|---|---|---|---|---|---|
| Vermiculite[1] | % | 25 | 50 | 75 | 100 | 125 | — |
| | kg/ton of seed | 5.0 | 10.0 | 15.0 | 20.0 | 25.0 | — |
| Sodium salt of carboxymethyl cellulose[2] | % | 0.5 | 1.0 | 2.0 | 3.0 | 3.5 | — |
| | kg/ton of seed | 0.10 | 0.20 | 0.40 | 0.60 | 0.70 | — |
| Chitosan[3] | % | 0.0005 | 0.005 | 0.0100 | 0.025 | 0.500 | — |
| | kg/ton of seed | 0.0001 | 0.001 | 0.002 | 0.005 | 0.100 | — |
| Roslin[4] | % | 1.25 | 2.50 | 5.00 | 7.50 | 10.00 | — |
| | kg/ton of seed | 0.25 | 0.50 | 1.00 | 1.5 | 2.0 | — |
| Topsin M[5] | % | 0.5 | 2.5 | 5.0 | 7.5 | 10.0 | — |
| | kg/ton of seed | 0.10 | 0.50 | 1.00 | 1.50 | 2.00 | — |
| Molybdenum salts[6] | % | 0.5 | 1.25 | 1.75 | 2.50 | 5.0 | — |
| | kg/ton of seed | 0.10 | 0.25 | 0.35 | 0.50 | 1.00 | — |
| Manganese salts[7] | % | 0.50 | 1.75 | 2.25 | 3.00 | 5.00 | — |
| | kg/ton of seed | 0.10 | 0.35 | 0.45 | 0.60 | 1.00 | — |
| Zinc salts[8] | % | 0.50 | 1.00 | 2.00 | 3.75 | 5.00 | — |
| | kg ton of seed | 0.10 | 0.20 | 0.40 | 0.75 | 1.00 | — |
| Gulliver ®[9] | % | 0.050 | 0.200 | 0.275 | 0.375 | 0.500 | — |
| | kg/ton of seed | 0.05 | 0.09 | 0.11 | 0.15 | 0.30 | — |

TABLE 1-continued

Concentration of Nanochip Components and Composition for Presowing Processing of Rice Seed

| Component | | Content of Components in Various Preparation Preparation Variant | | | | | |
|---|---|---|---|---|---|---|---|
| | | 1 | 2 | 3 | 4 | 5 | Control |
| Water | % | balance | balance | balance | balance | balance | — |
| | L/ton of seed | 15 | 17 | 20 | 22 | 25 | — |

[1]Vermiculite (carrier for biologically active component; comprises a natural mineral that expands with heat application)
[2]Sodium salt of carboxymethyl cellulose (polymeric binder; water-soluble polymer)
[3]Roslin (plant-growth regulator - copolymer of nitron fibers with nitrolignin)
[4]Chitosan (linear polysaccharide composed of randomly distributed β-(1-4)-linked D-glucosamine (deacetylated unit) and N-acetyl-D-glucosamine (acetylated unit); in agriculture, chitosan is used primarily as a natural seed treatment and plant-growth enhancer and as a substance that boosts the ability of plants to defend against fungal infections)
[5]Topsin M (Fungicide - dimethyl 4,4'-o-phenylenebis[3-thioallopahnate])
[6]Molybdenum salts (nutritive microelement)
[7]Manganese salts (nutritive microelement)
[8]Zinc salts (nutritive microelement)
[9]Gulliver ® (herbicide produced by DuPont Company; contains active constituent of sulfonylurea compound)

The effect of treating rice seed with biologically active nanochips of different compositions on sowing properties and yield is shown in Table 2.

TABLE 2

Characteristics of Sowing Properties of Rice Seed Treated with Biologically Active Nanochips, Weed-suppressing Capacity, and Effect on Rice Yield

| Characteristic | Preparation Variant | | | | | |
|---|---|---|---|---|---|---|
| | 1 | 2 | 3 | 4 | 5 | КОНТрОЛЬ |
| Germination capacity, % | 37.4 | 42.6 | 50.5 | 45.2 | 34.6 | 30.2 |
| Suppression of pathogens, % | 61.0 | 75.1 | 81.5 | 80.4 | 84.3 | — |
| Suppression of weeds: | | | | | | |
| Echinochloa | 30.0 | 93.4 | 95.1 | 96.3 | 97.2 | — |
| Bbulboschoenus | 89.6 | 95.0 | 96.0 | 96.0 | 97.0 | — |
| Yield, centner*/hectare | 34.3 | 41.2 | 43.3 | 42.1 | 30.4 | 36.3 |

*Centner corresponds to 100 kg of product weight

Thus, as can be seen from Table 2, the following component contents (kg/ton of seed) can be recommended for biologically active nanochips intended for presowing treatment of rice seed:
Vermiculite: 10 to 20 kg
Sodium salt of carboxymethyl cellulose: 0.20 to 0.60 kg
Chitosan: 0,001 to 0.005 kg
Roslin: 0.50 to 1.5 kg
Topsin M: 0.50 to 1.5 kg
Molybdenum salts: 0.25 to 0.50 kg
Manganese salts: 0.35 to 0.60 kg
Zinc salts: 0.20 to 0.75 kg
Gulliver®: 0.09 to 0.15 kg, and
Water: 15 to 25 liters Compared with the control group, variants 1 and 5 did not provide optimal contents of the biologically active nanochip components with regard to seed germination, suppression of pathogens, suppression of weeds, and improvement of yield.

EXAMPLE 2

Composition of Biologically Active Nanochip for Wheat Seed Preparation for Planting Wheat seeds (see Tables 3 and 4) precalibrated and pre-sorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelleting drum by spraying nanochip-containing finely dispersed homogeneous colloidal system (or solution) with a dosing device (based on 10 mL of solution per 1 kg of seeds) for 2 to 3 sec. The nanochip compositions were prepared in five different variants, as shown in Table 3.

To form and fix the biologically active nanochips on the surfaces of seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

TABLE 3

Concentration of Nanochip Components and their Composition for Presowing Treatment of Wheat Seeds

| Component | Units | Contents of Components in Various Preparation Preparation Variant | | | | | |
|---|---|---|---|---|---|---|---|
| | | 1 | 2 | 3 | 4 | 5 | Control |
| Kaolin[1] | % | 50 | 100 | 200 | 250 | 350 | — |
| | kg/ton of seeds | 5.0 | 10.0 | 20.0 | 25.0 | 35.0 | — |

TABLE 3-continued

Concentration of Nanochip Components and their
Composition for Presowing Treatment of Wheat Seeds Contents of Components in Various Preparation
Preparation Variant

| Component | Units | 1 | 2 | 3 | 4 | 5 | Control |
|---|---|---|---|---|---|---|---|
| Polyvinyl alcohol[2] | % | 0.75 | 1.00 | 1.50 | 2.00 | 3.00 | — |
| | Kg/ton of seeds | 0.075 | 0.10 | 0.15 | 0.20 | 0.30 | — |
| Pectin[3] | % | 0.5 | 1.0 | 1.5 | 2.5 | 4.0 | — |
| | kg/ton of seeds | 0.05 | 0.10 | 0.15 | 0.25 | 0.40 | — |
| Sodium gummate[4] | % | 2.5 | 5.0 | 7.0 | 9.0 | 12.0 | — |
| | kg/ton of seeds | 0.25 | 0.50 | 0.70 | 0.9 | 1.2 | — |
| Lamardor ®[5] | % | 0.25 | 1.00 | 1.50 | 2.00 | 2.50 | — |
| | kg/ton of seeds | 0.025 | 0.10 | 0.15 | 0.20 | 0.25 | — |
| Copper salts[6] | % | 0.050 | 0.075 | 0.100 | 0.300 | 0.500 | — |
| | kg/ton of seeds | 0.0050 | 0.0075 | 0.0100 | 0.0300 | 0.0500 | — |
| Boron[7] | % | 0.005 | 0.009 | 0.010 | 0.050 | 0.100 | — |
| | kg ton of seeds | 0.0005 | 0.0009 | 0.0010 | 0.0050 | 0.0100 | — |
| Sericine[8] | % | 0.01 | 0.10 | 0.20 | 0.50 | 1.00 | — |
| | kg/ton of seeds | 0.001 | 0.01 | 0.02 | 0.05 | 0.100 | — |
| Granstar ®[9] | % | 0.5 | 0.90 | 1.1 | 1.5 | 3.0 | — |
| | Kg/ton of seeds | 0.010 | 0.040 | 0.055 | 0.750 | 1.000 | — |
| Water | % | balance | balance | balance | balance | balance | — |
| | L/ton of seeds | 7 | 8 | 10 | 12 | 14 | — |

[1]Kaolin (carrier)
[2]Polyvinyl alcohol (polymeric binder)
[3]Pectin (structural biodegradable heteropolysaccharide contained in the primary cell walls of terrestrial plants)
[4]Sodium gummate (plant-growth regulator)
[5]Lamardor ® (treatment fungicide; prothioconazole plus tebuconazole)
[6]Copper salts (nutritive microelement)
[7]Boron (nutritive microelement)
[8]Sericine (natural water-soluble biopolymer having high content of oxyamino acids)
[9]Granstar ® (herbicide used to control broad-leaved weeds in wheat and barley)

The effect of treating the seeds with biologically active nanochips of different compositions on sowing properties and yield is shown in Table 4.

TABLE 4

Characteristics of Sowing Properties, Productivity, and
Biochemical Characteristics of Wheat Seed Treated with Biologically
Active Nanochips, Effect on Productivity, and Biochemical
Characteristics of Food Products Obtained from Treated Wheat

| Characteristics | Preparation Variants | | | | | |
|---|---|---|---|---|---|---|
| | 1 | 2 | 3 | 4 | 5 | Control |
| Laboratory germination, % | 80.5 | 92.5 | 95.5 | 90.3 | 85.0 | 78.9 |
| Yield, t/ha | 2.65 | 2.85 | 3.00 | 2.90 | 2.76 | 2.70 |
| Protein content in: | | | | | | |
| Seeds, % | 12.4 | 12.8 | 13.4 | 13.0 | 12.8 | 12.0 |
| Gluten, % | 24.0 | 24.1 | 24.5 | 24.4 | 24.3 | 24.0 |

As seen in Table 4 in variants 1 to 5, wheat seeds treated with biologically active nanochips of the invention showed improvement in germination and content of protein and gluten.

The following contents (kg/ton of seeds) of the nanochip components can be recommended for presowing treatment of wheat seeds:

Kaolin: 5.0 to 35.0 kg
Polyvinyl alcohol: 0.075 to 0.30 kg
Pectin: 0.05 to 0.40 kg
Sodium gummate: 0.25 to 1.2 kg
Lamardor®: 0.025 to 0.25 kg
Sericine: 0.005 to 0.05 kg
Boron: 0.0005 to 0.01 kg
Copper salts: 0.001 to 0.1 kg
Granstar®: 0.01 to 1.0 kg, and
Water: 7 to 14 liters

EXAMPLE 3

Composition of Biologically Active Nanochip for Cotton Seed Preparation for Planting Cotton seeds (see Tables 5 and 6) precalibrated and pre-sorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 30 mL of solution per 1 kg of seeds) for 2 to 3 sec. The nanochips compositions were prepared in five different variants, as shown in Table 5.

TABLE 5

Concentration of Nanochip Components and their Composition for Presowing Processing of Cotton Seed

| Component | Unit | 1 | 2 | 3 | 4 | 5 | Control |
|---|---|---|---|---|---|---|---|
| Lignin[1] | % | 16.7 | 33.3 | 50.0 | 66.7 | 166.7 | — |
|  | kg/ton of seeds | 5.0 | 10.0 | 15.0 | 20.0 | 50.0 | — |
| Oxyethyl cellulose[2] | % | 0.33 | 1.67 | 2.00 | 2.67 | 3.33 | — |
|  | kg/ton of seeds | 0.10 | 0.50 | 0.60 | 0.80 | 1.0 | — |
| Cruiser ®[3] | % | 3.3 | 10.0 | 13.3 | 16.7 | 33.3 | — |
|  | kg/ton of seeds | 1.0 | 3.0 | 4.0 | 5.0 | 10.0 | — |
| Panoctine ®[4] | % | 1.67 | 6.67 | 13.33 | 23.33 | 33.33 | — |
|  | kg/ton of seeds | 0.5 | 2.0 | 4.0 | 7.0 | 10.0 | — |
| Extrasol[5] | % | 0.33 | 1.67 | 3.33 | 6.67 | 16.67 | — |
|  | kg/ton of seeds | 0.10 | 0.50 | 1.00 | 2.00 | 5.00 | — |
| Iron hydroxy-acetate[6] | % | 0.00033 | 0.0033 | 0.0100 | 0.0167 | 0.0267 | — |
|  | kg/ton of seeds | 0.0001 | 0.0010 | 0.0030 | 0.0050 | 0.0080 | — |
| Vitawax ®[7] | % | 3.33 | 6.67 | 10.00 | 16.67 | 33.33 | — |
|  | kg/ton of seeds | 1.0 | 2.0 | 3.0 | 5.0 | 10.0 | — |
| Water | % | balance | balance | balance | balance | balance | — |
|  | L/ton of seeds | 20 | 22 | 25 | 30 | 35 |  |

[1]Lignin (carrier for biologically active component; a complex chemical compound most commonly derived from wood; organic polymer)
[2]Oxyethyl cellulose (polymeric binder; derivative of natural polysaccharide)
[3]Cruiser ® (insecticide; active ingredient in Cruiser, thiamethoxam, a systemic insecticide in neonicotinoid class of chemicals)
[4]Panoctine ® (nonvolatile liquid seed treatment for control of certain seed-borne diseases; used as solution containing guazatine)
[5]Extrasol (plant extract; nitrogen-fixing fertilizer; increases germinating power of seeds; improves absorption of nutrient elements by plants)
[6]Iron hydroxyacetate (growth stimulator)
[7]Vitawax ® (seed-treatment fungicide effective against early-season diseases; contains carboxyn, a systemic fungicide)

To form and fix the biologically active nanochips on the surfaces of the seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

The effect of treating seeds with biologically active nanochips of different compositions on sowing properties and yield is shown in Table 6.

TABLE 6

Characteristics of Sowing Properties of Cotton Seeds Treated with Biologically Active Nanochips and Effect of Nanochip Composition on Yield of Sugar Beets

| Characteristic | Preparation Variant | | | | | |
|---|---|---|---|---|---|---|
|  | 1 | 2 | 3 | 4 | 5 | Control |
| Germination energy, % | 85.0 | 90.3 | 92.8 | 90.0 | 80.6 | 80.1 |
| Laboratory germination, % | 93.0 | 95.1 | 96.9 | 92.4 | 88.0 | 85.0 |
| Yield, centner/hectare | 32.7 | 33.0 | 35.2 | 32.0 | 31.5 | 30.0 |

As seen in Table 6 in variants 1 to 5, cotton seeds treated with biologically active nanochips of the invention showed improvement in germination and yield.

The following ranges of nanochip components (kg/ton of seeds) can be recommended for presowing treatment of cotton seed:

Lignin: 5.0 to 50.0 kg
Oxyethyl cellulose: 0.1 to 1.0 kg
Iron hydroxyacetate: 0.0001 to 0.008 kg
Cruiser®: 1.0 to 10.0 kg
Panoctine®: 0.5 to 10.0 kg
Extrasol: 0.1 to 5.0 kg
Vitawax®: 1.0 to 10.0 kg
Water: 25 to 30 liters

EXAMPLE 4

Composition of Biologically Active Nanochips for Sugar Beet Seed Preparation for Planting Sugar beet seeds (see Tables 7 and 8) precalibrated and presorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 40 mL of solution per 1 kg of seeds) for 2 to 3 sec. The biologically active nanochip compositions were prepared in five different variants, as shown in Table 7.

To form and fix the biologically active nanochips on the surfaces of the seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

be recommended for biologically active nanochips intended for presowing treatment of sugar beet seeds:
Vermiculite: 5.0 to 100 kg
Polyethylene glycol: 0.1 to 2.0 kg

TABLE 7

Concentration of Nanochip Components and their Composition for Presowing Processing

| Component | Units | Content of Biologically Active Nanochips Variants | | | | | Control |
|---|---|---|---|---|---|---|---|
| | | 1 | 2 | 3 | 4 | 5 | |
| Vermiculite[1] | % | 12.5 | 25.0 | 75.0 | 125.0 | 250.0 | — |
| | kg/ton of seeds | 5.0 | 10.0 | 30.0 | 50.0 | 100.0 | |
| Polyethylene glycol[2] | % | 0.25 | 1.25 | 2.00 | 2.50 | 5.00 | — |
| | kg/ton of seeds | 0.10 | 0.50 | 0.80 | 1.00 | 2.0 | |
| Heteroauxin[3] | % | 0.0025 | 0.0050 | 0.0075 | 0.0125 | 0.0250 | — |
| | kg/ton of seeds | 0.001 | 0.002 | 0.003 | 0.005 | 0.0100 | |
| Unigol ®[4] | % | 0.125 | 0.250 | 0.500 | 1.250 | 2.500 | — |
| | kg/ton of seeds | 0.05 | 0.10 | 0.20 | 0.5 | 1.0 | |
| Impact ®[5] | % | 0.125 | 0.250 | 0.500 | 1.250 | 2.500 | — |
| | kg ton of seeds | 0.05 | 0.10 | 0.20 | 0.50 | 1.00 | |
| Fury ®[6] | % | 0.025 | 0.062 | 0.175 | 0.225 | 0.250 | — |
| | kg/ton of seeds | 0.010 | 0.025 | 0.070 | 0.090 | 0.100 | |
| Caribou ®[7] | % | 0.0050 | 0.0075 | 0.0100 | 0.0125 | 0.0150 | — |
| | kg/ton of seeds | 0.125 | 0.250 | 0.375 | 0.625 | 1.250 | |
| Water | % | balance | balance | balance | balance | balance | — |
| | L/ton of seeds | 35 | 37 | 40 | 42 | 45 | |

[1]Vermiculite (carrier for biologically active component; comprises a natural mineral that expands with the application of heat)
[2]Polyethylene glycol (polymeric binder)
[3]Heteroauxin (a growth-promoting hormone, 3-indoleacetic acid, occuring in some plants)
[4]Unigol ® (nutritive fertilizer; comprises salts of nitrogen, phosphorus, and potassium enriched with nutritive microelements)
[5]Impact ® (flutriafol - one of very few compounds to reach and disinfect the embryo of a seed; systemic fungicide used against fungal pathogens in beets, cereals, etc.)
[6]Fury ® (insecticide; zeta-cypermethrin)
[7]Caribou ® (herbicide of DuPont Co.; contains triflusulfuron)

The effect of treating the seeds with the biologically active nanochips of different compositions on sowing properties and yield is shown in Table 8.

TABLE 8

Characteristics of Sowing Properties of Sugar Beet Seeds Treated with Biologically Active Nanochips, Yield, Productivity, and Effect of Nanochip Component Content on Content of Sugar in the Sugar Beet

| Characteristic | Nanochip Component Content Variant | | | | | Control |
|---|---|---|---|---|---|---|
| | 1 | 2 | 3 | 4 | 5 | |
| Germination energy, % | 68.9 | 69.1 | 71.5 | 69.5 | 68.3 | 70.7 |
| Laboratory germination, % | 86.3 | 87.51 | 89.8 | 84.5 | 81.9 | 75.5 |
| Field germination, % | 64.6 | 65.6 | 74.5 | 68.4 | 67.3 | 50.0 |
| Yield, centner/hectare | 48.3 | 51.7 | 55.5 | 53.2 | 50.4 | 48.3 |
| Sugar recovery, ton/hectare | 7.47 | 7.59 | 8.41 | 7.97 | 7.50 | 7.28 |

It can be seen in Table 8 that the contents of biologically active nanochips as shown in Variants 1 to 5 of Table 7 provide higher sugar recovery than the control group of untreated seeds. Therefore, the following contents (kg/ton of seeds) can Heteroauxin: 0.001 to 0.01 kg
Impact®: 0.05 to 1.0 kg
Fury®: 0.01 to 0.1 kg
Caribou®: 0.125 to 0.250 kg
Water: 35 to 45 liters

EXAMPLE 5

Composition of Biologically Active Nanochip for Soybean Seed Preparation for Planting Soybean seeds (see Tables 9 and 10) precalibrated and presorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 15 mL of solution per 1 kg of seeds) for 2 to 3 sec. The nanochips compositions were prepared in five different variants, as shown in Table 9.

For forming and fixing the biologically active nanochips on the surfaces of seeds, the treated seeds were tumbled and mixed for 5.0 min. in the pelletizer and then unloaded to a feed screw where during transportation the treated seeds were dried in a flow of air heated to 20-30° C. Following this, the seeds were fed to a receiving hopper, packaged, and sent to storage until sowing.

seeds) can be recommended for biologically active nanochips intended for presowing treatment of soybean seeds:
Pearlite: 3.0 to 25.0 kg
Polyvinyl alcohol: 0.10 to 1.0 kg

TABLE 9

Concentration of Nanochip Components and their Compositions for Presowing Processing

| Component | Units | Content of Nanochip Component Variants | | | | | Control |
|---|---|---|---|---|---|---|---|
| | | 1 | 2 | 3 | 4 | 5 | |
| Perlite[1] | % | 20.0 | 33.3 | 66.7 | 100.0 | 166.7 | — |
| | Kg/ton of seeds | 3.0 | 5.0 | 10.0 | 15.0 | 25.0 | — |
| Polyvinyl alcohol[2] | % | 0.67 | 1.67 | 3.00 | 4.00 | 2.50 | — |
| | Kg/ton of seeds | 0.10 | 0.25 | 0.45 | 0.60 | 1.00 | — |
| Albit[3] | % | 0.067 | 0.167 | 0.267 | 0.600 | 1.000 | — |
| | Kg/ton of seeds | 0.010 | 0.025 | 0.04 | 0.09 | 0.15 | — |
| Baikal EM-1[4] | % | 0.013 | 0.13 | 0.267 | 0.400 | 0.667 | — |
| | Kg/ton of seeds | 0.002 | 0.02 | 0.04 | 0.06 | 0.100 | — |
| Terpenol[5] | % | 0.0067 | 0.0167 | 0.0333 | 0.0667 | 0.3333 | — |
| | Kg/ton of seeds | 0.0010 | 0.0025 | 0.0050 | 0.010 | 0.050 | — |
| Boron salts[6] | % | 0.067 | 0.667 | 1.333 | 2.000 | 6.667 | — |
| | Kg/ton of seeds | 0.01 | 0.1 | 0.2 | 0.3 | 1.0 | — |
| Molybdenum salts[7] | % | 0.67 | 1.33 | 2.00 | 3.33 | 6.67 | — |
| | Kg/ton of seeds | 0.1 | 0.2 | 0.3 | 0.5 | 1.0 | — |
| Frontier ®[8] | % | 0.67 | 1.67 | 3.67 | 5.00 | 6.67 | — |
| | Kg/ton of seeds | 0.10 | 0.25 | 0.55 | 0.75 | 1.0 | — |
| Water[9] | % | balance | balance | balance | balance | balance | — |
| | L/ton of seeds | 10 | 12 | 15 | 17 | 20 | — |

[1]Perlite (carrier for biologically active nanochips)
[2]Polyvinyl alcohol (binder)
[3]Albit (growth-control regulator)
[4]Baikal EM-1 (biofertilizer)
[5]Terpenol (plant-growth regulator)
[6]Boron salts (nutritive component)
[7]Molybdenum salts (nutritive component)
[8]Frontier ® (herbicide)
[9]Water (solvent)

The effect of treating seeds with biologically active nanochips of different compositions on sowing properties and yield is shown in Table 10.

TABLE 10

Characteristics of Sowing Properties, Productivity, and Biochemical Characteristics of Soybean Seeds Treated with Biologically Active Nanochips, and Effect of Treatment on Productivity and Nutritive Characteristics of Food Products Obtained from Treated Soybeans

| Characteristic | Content of Nanochip Component Variants | | | | | Control |
|---|---|---|---|---|---|---|
| | 1 | 2 | 3 | 4 | 5 | |
| Laboratory germination, % | 1.40 | 1.45 | 1.55 | 1.50 | 1.42 | 1.10 |
| Yield, tone/hectare | 40.0 | 41.5 | 43.0 | 42.5 | 41.8 | 39.5 |
| Protein content in seeds, % | | | | | | |

It can be seen in Table 10 that the contents of biologically active nanochips as shown in Variants 1 to 5 in Table 9 provide higher yield and protein content than the control group of untreated seeds. Therefore, the following contents (kg/ton of Albit: 0.01 to 0.15 kg
Terpenol: 0.005 to 0.01 kg
Boron salt: 0.01 to 1.0 kg
Molybdenum salts: 0.1 to 1.0 kg
Frontier®: 0.1 to 1.0 kg
Baikal EM-1 1 kg
Water: 10 to 20 liters

EXAMPLE 6

Composition of Biologically Active Nanochip for Corn Seed Preparation for Planting Corn seed (see Tables 11 and 12) precalibrated and presorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 30 mL of solution per 1 kg of seeds) for 2 to 3 sec. The biologically active nanochips compositions were prepared in five different variants, as shown in Table 11.

To form and fix the biologically active nanochips on the surfaces of the seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

TABLE 11

Concentration of Nanochip Components and their Composition for Presowing Processing of Corn Seed

| Component | Unit | Content of Nanochip Component Variants | | | | | Control |
|---|---|---|---|---|---|---|---|
| | | 1 | 2 | 3 | 4 | 5 | |
| Peat[1] | % | 3.75 | 4.00 | 4.25 | 4.50 | 4.71 | — |
| | Kg/ton of seeds | 10.0 | 20.0 | 25.0 | 40.0 | 50.0 | — |
| Polyvinyl-pyrrolidone[2] | % | 0.0050 | 0.0075 | 0.0100 | 0.0125 | 0.0150 | — |
| | Kg/ton of seeds | 0.01 | 0.25 | 0.40 | 0.80 | 1.00 | — |
| Sodium salt of carboxymethyl cellulose[3] | % | 0.0050 | 0.0075 | 0.0100 | 0.0125 | 0.0150 | — |
| | Kg/ton of seeds | 0.1 | 0.2 | 0.4 | 0.8 | 1.0 | — |
| Nicotinic acid[4] | % | 0.0050 | 0.0075 | 0.0100 | 0.0125 | 0.0150 | — |
| | Kg/ton of seeds | 0.25 | 0.50 | 0.70 | 0.9 | 1.2 | — |
| Unum[5] | % | 0.0050 | 0.0075 | 0.0100 | 0.0125 | 0.0150 | — |
| | | 0.0005 | 0.0010 | 0.0020 | 0.0050 | 0.0100 | — |
| Vitawax[6] | % | 0.0050 | 0.0075 | 0.0100 | 0.0125 | 0.0150 | — |
| | Kg/ton of seeds | 0.5 | 1.0 | 1.5 | 2.0 | 5.0 | — |
| Titus[7] | % | 0.0050 | 0.0075 | 0.0100 | 0.0125 | 0.0150 | — |
| | Kg/ton of seeds | 0.050 | 0.150 | 0.220 | 0.300 | 0.400 | — |
| Water | balance | balance | balance | balance | balance | balance | — |
| | L/ton of seeds | 25 | 27 | 30 | 32 | 34 | — |

[1]Peat (carrier for biologically active components)
[2]Polyvinyl pyrrolidone (water-soluble polymeric binder)
[3]Sodium salt of carboxymethyl cellulose (water-soluble polymeric binder)
[4]Nicotinic acid (seed-germination stimulator)
[5]Unum (biofertilizer; arachidonic acid)
[6]Vitavax (Carboxine plus Thiram; widely used seed treatment fungicide effective against early-season diseases)
[7]Titus (herbicide; rimsulfuron)

The effect of treating corn seeds with biologically active nanochips of different compositions on sowing properties and yield is shown in Table 12.

TABLE 12

Characteristics of Sowing Properties, Productivity, and Biochemical Characteristics of Corn Seeds Treated with Biologically Active Nanochips, and Effect of Treatment on Yield and Nutritive Characteristics of Food Products Obtained from Treated Corn

| Characteristic | Content of Nanochip Component Variants | | | | | Control |
|---|---|---|---|---|---|---|
| | 1 | 2 | 3 | 4 | 5 | |
| Germination energy, % | 90.0 | 91.5 | 93.5 | 92.1 | 89.0 | 92.0 |
| Laboratory germination, % | 92.5 | 93.5 | 95.0 | 92.5 | 91.0 | 90.0 |
| Field germination, % | 89.0 | 91.1 | 92.5 | 91.0 | 90.0 | 85.0 |
| Yield, ton/hectare | 62.5 | 63.6 | 68.0 | 67.0 | 64.1 | 61.9 |
| Grain yield, % | 81.0 | 82.0 | 83.5 | 80.0 | 79.0 | 79.5 |

It can be seen in Table 12 that the contents of biologically active nanochips as shown in Variants 1 to 4 in Table 11 provide a higher yield of grain than the control group of untreated seeds. Therefore, the following contents (kg/ton of seeds) can be recommended for biologically active nanochips intended for presowing treatment of corn seeds:

Peat: 10.0 to 40 kg
Polyvinyl pyrrolidone: 0.01 to 0.80 kg
Sodium salt of carboxymethyl cellulose: 0.1 to 0.8 kg
Nicotinic acid: 0.25 to 0.9 kg
Unum: 0.005 kg
Vitavax: 0.5 to 2.0 kg
Titus: 0.05 to 0.3 kg
Water: 25 to 35 liters

EXAMPLE 7

Composition of Biologically Active Nanochips for Tomato-Seed Preparation for Planting Corn seed (see Tables 13 and 14) precalibrated and presorted by passing through Petkus sieves of different cell diameters (depending on seed dimensions) were fed to an accumulation hopper in the amount of 100 kg, from where the seeds were periodically unloaded in small portions under gravity onto a rotary pelletizer drum. The surfaces of the seeds were coated in the pelletizer drum by spraying the nanochip-containing finely dispersed homogeneous colloidal system (or solution) with a dosing device (based on 15 mL of solution per 1 kg of seeds) for 2 to 3 sec. The nanochip compositions were prepared in five different variants, as shown in Table 13.

To form and fix the biologically active nanochips on the surfaces of the seeds, the treated seeds were tumbled and mixed for 5 min. in the pelletizer and were then unloaded to a feed screw where during transportation the treated seeds were dried in a flow of air heated to 20 to 30° C. Following this, the seeds were fed to a receiving hopper, packaged, and sent to storage until sowing.

seeds) can be recommended for biologically active nanochips intended for presowing treatment of tomato seeds:
Diatomite: 10 to 25 kg
Chitosan: 0.10 to 0.20 kg

TABLE 13

Concentration of Nanochip Components and Compositions for Presowing Processing of Tomato Seeds

| Component | Unit | Content of Nanochip Component Variants | | | | | Control |
|---|---|---|---|---|---|---|---|
| | | 1 | 2 | 3 | 4 | 5 | |
| Diatomite[1] | % | 3.75 | 4.00 | 4.25 | 4.50 | 4.71 | — |
| | kg/ton of seeds | 5.0 | 10.0 | 20.0 | 25.0 | 35.0 | — |
| Chitosan[2] | % | 0.0050 | 0.0075 | 0.0100 | 0.0125 | 0.0150 | — |
| | kg/ton of seeds | 0.075 | 0.10 | 0.15 | 0.20 | 0.30 | — |
| Glutamic acid[3] | % | 0.0050 | 0.0075 | 0.0100 | 0.0125 | 0.0150 | — |
| | kg/ton of seeds | 0.05 | 0.10 | 0.15 | 0.25 | 0.40 | — |
| Succinic acid[4] | % | 0.0050 | 0.0075 | 0.0100 | 0.0125 | 0.0150 | — |
| | kg/ton of seeds | 0.25 | 0.50 | 0.70 | 0.9 | 1.2 | — |
| Biological humus[5] | % | 0.0050 | 0.0075 | 0.0100 | 0.0125 | 0.0150 | — |
| | kg/ton of seeds | 0.025 | 0.10 | 0.15 | 0.20 | 0.25 | — |
| Akrobat ®[6] | % | 0.0050 | 0.0075 | 0.0100 | 0.0125 | 0.0150 | — |
| | kg/ton of seeds | 0.0050 | 0.0075 | 0.0100 | 0.0300 | 0.0500 | — |
| Karate[7] | % | 0.0050 | 0.0075 | 0.0100 | 0.0125 | 0.0150 | — |
| | kg/ton of seeds | 0.0005 | 0.0009 | 0.0010 | 0.0050 | 0.0100 | — |
| Water | % | balance | balance | balance | balance | balance | — |
| | L/ton of seeds | 10 | 12 | 15 | 17 | 20 | — |

[1]Diatomite (diatomaceous earth; carrier for biologically active component)
[2]Chitosan [linear polysaccharide composed of randomly distributed β-(1-4)-linked D-glucosamine (deacetylated unit) and N-acetyl-D-glucosamine (acetylated unit); in agriculture, chitosan is used primarily as a natural seed treatment and plant-growth enhancer and as a substance that boosts the ability of plants to defend against fungal infections]
[3]Glutamic acid (growth regulator)
[4]Succinic acid (growth stimulator)
[5]Biological humus (biofertilizer)
[6]Akrobat ® (fungicide that can control various crop diseases; acting component is dimethomorph)
[7]Karate (insecticide; Lamba-cigalotrin)

The effect of treating corn seeds with biologically active nanochips of different compositions on sowing properties and yield is shown in Table 14.

TABLE 14

Characteristics of Suppression Pathogens in Tomatoes Grown from Biologically Active Nanochip-Treated Seeds, Development of Root System, and Effect of Nanochip Compositions on Yield

| Characteristic | Content of Nanochip Component Variants | | | | | Control |
|---|---|---|---|---|---|---|
| | 1 | 2 | 3 | 4 | 5 | |
| Average size of nematode galls (mm²) | 17.4 | 17.0 | 13.2 | 13.8 | 16.8 | 19.2 |
| Average size of nematode females (mm²) | 0.295 | 0.258 | 0.250 | 0.254 | 0.270 | 0.320 |
| Weight of roots (g) | 5.0 | 6.0 | 7.5 | 7.4 | 5.3 | 4.4 |
| Yield (ton/hectare) | 48.0 | 59.6 | 62.1 | 61.4 | 49.0 | 50.0 |

It can be seen in Table 14 that the contents of biologically active nanochips as shown in Variants 2, 3, and 4 in Table 13 provide a higher yield of tomatoes than the control group of untreated seeds. Therefore, the following contents (kg/ton of Glutamic acid: 0.10 to 0.25 kg
Succinic acid: 0.50 to 0.90 kg
Biological humus: 0.10 to 0.20 kg
Akrobat®: 0.0075 to 0.03 kg
Karate: 0.0005 to 0.005 kg
Water: 10 to 20 liters Thus, it has been shown that the invention provides biologically active multifunctional nanochips and a method for application for production of high-quality seeds. The aforementioned nanochips are pretreated for sowing on the basis of nanotechnology that enhances seed and plant adaptability to real-life adverse environmental conditions and are constructed as multifunctional nanochips that are integrated in the nanopores of the seed cover. The method for presowing treatment of the seeds is based on a prediction of adverse effects on plant growing, and the composition and properties of the biologically active nanochips can be modified by populating pores of carriers with appropriate biologically active nanoparticles and phytosanitary nanoparticles, which enhance plant tolerance to new adverse environmental factors, improve germination properties, and increase yield and productivity. The chips and method of the invention: extend seed dormancy, allow the planting seeds to be stored for a long time without compromising quality, initialize termination of seed dormancy under changing environmental conditions by using variously composed and structured biologically active nanochips before planting, enhanced seed germination, and enhanced seed tolerance to pathogens, salinization, draught, frost, and other adverse environmental effects, increase yield, improve produce quality, reduce the rate of consumption of physiologically active and phytosanitary components, and easily adapt to currently existing technologies of seed preparation for planting.

Although the invention has been shown and described with reference to specific practical examples, it is understood that these examples should not be construed as limiting the fields of practical application and that any changes and modifications are possible without departure from the scope of the attached claims. For example, the principle of the invention is applicable to treating seeds of other agricultural plants with other nanochip compositions specifically selected for those specific agricultural plants and growing conditions.

The invention claimed is:

1. Biologically active nanochips for treating seeds of agricultural plants in order to improve germination conditions of seeds and development of plants and for protecting plants from anticipated and averaged adverse conditions, said biologically active nanochips comprising at least one of each of the following:
   carrier for carrying physiologically active components;
   biologically active component carried by said carrier and selected from a group comprising at least one of each of the following:
      binder;
      nanochip stabilizer;
      herbicide;
      plant-growth regulator;
      seed-germination stimulator;
      fungicide;
      bactericide;
      fertilizer;
      nutritive component; and
      solvent;
   wherein at least one carrier and at least one biologically active component being indispensable components of the biologically active nanochips and the other biologically active components being selected and included with reference to said anticipated and averaged adverse conditions; said at least one carrier having pores capable of accommodating the biologically active nanochips or surfaces capable of holding the biologically active nanochips.

2. The biologically active nanochip according to claim 1 for treating rice seeds, comprising the following components in the amounts per 1 ton of seeds: vermiculite in the amount of 10 to 20 kg for use as the carrier, sodium salt of carboxymethyl cellulose in the amount of 0.20 to 0.60 kg for use as a binder; chitosan in the amount of 0.001 to 0.005 kg for use as a bactericide and a plant-growth regulator; Roslin in the amount of 0.50 to 1.5 kg for use as a plant-growth regulator; Topsin-M in the amount of 0.50 to 1.5 kg for use as a fungicide; molybdenum salts in the amount of 0.25 to 0.50 kg for use as a nutritive component; manganese salts in the amount of 0.35 to 0.60 kg for use as a nutritive component; zinc salts in the amount of 0.20 to 0.75 kg for use as a nutritive component; Gulliver® in the amount of 0.09 to 0.15 kg for use as a herbicide; and 15 to 25 liters of water for use as a solvent.

3. The biologically active nanochip according to claim 1 for treating wheat seeds, comprising the following components in the amounts per 1 ton of seeds: Kaolin in the amount of 5.0 to 35.0 kg for use as the carrier; polyvinyl alcohol in the amount of 0.075 to 0.30 kg for use as a binder; pectin in the amount of 0.05 to 0.40 kg for use as a nanochip stabilizer; sodium gummate in the amount of 0.25 to 1.2 kg for use as a plant-growth regulator; Lamardor® in the amount of 0.025 to 0.25 kg for use as a fungicide; Sericine in the amount of 0.005 to 0.05 kg for use as a binder; boron in the amount of 0.0005 to 0.01 kg for use as a nutritive component; copper salts in the amount of 0.001 to 0.1 kg for use as a nutritive component; Granstar® for use as a herbicide in the amount of 0.01 to 1.0 kg; and 7 to 14 liters of water for use as a solvent.

4. The biologically active nanochip according to claim 1 for treating cotton seeds, comprising the following components in the amounts per 1 ton of seeds: lignin in the amount of 5.0 to 50.0 kg for use as a carrier; oxyethyl cellulose in the amount of 0.1 to 1.0 kg for use as a binder; iron hydroxyacetate in the amount of 0.0001 to 0.008 kg for use as a plant-growth regulator; Cruiser® in the amount of 1.0 to 10.0 kg for use as an insecticide; Panoctine® in the amount of 0.5 to 10.0 kg for use as a bactericide; Extrasol in the amount of 0.1 to 5.0 kg for use as a fertilizer; Vitawax® in the amount of 1.0 to 10.0 kg for use as a fungicide; and 25 to 35 liters of water for use as a solvent.

5. The biologically active nanochip according to claim 1 for treating sugar beet seeds, comprising the following components in the amounts per 1 ton of seeds: vermiculite in the amount of 5.0 to 100 kg for use as a carrier; polyethylene glycol in the amount of 0.1 to 2.0 kg for use as a binder; Heteroauxin in the amount of 0.001 to 0.01 kg for use as a plant-growth regulator; Impact® in the amount of 0.05 to 1.0 kg for use as a fungicide; Fury® in the amount of 0.01 to 0.1 kg for use as an insecticide; Unigol® in the amount of 0.05 to 1.0 kg for use as a nutritive component; Caribou® in the amount of 0.125 to 0.250 kg for use as an herbicide; and 35 to 45 liters of water for use as a solvent.

6. The biologically active nanochip according to claim 1 for treating soybean seeds, comprising the following components in the amounts per 1 ton of seeds: perlite in the amount of 3.0 to 25.0 kg; polyvinyl alcohol in the amount of 0.10 to 1.0 kg; Albit in the amount of 0.01 to 0.15 kg; Terpenol in the amount of 0.005 to 0.01 kg; Boron salts in the amount of 0.01 to 1.0 kg; molybdenum salts in the amount of 0.1 to 1.0 kg; Frontier® in the amount of 0.1 to 1.0 kg; Baikal EM-1 kg, and 10 to 15 liters of water for use as a solvent.

7. The biologically active nanochip according to claim 1 for treating corn seeds, comprising the following components in the amounts per 1 ton of seeds: peat in the amount of 10.0 to 40 kg for use as a carrier; polyvinyl pyrrolidone in the amount of 0.01 to 0.80 kg for use as binder; sodium salt of carboxymethyl cellulose in the amount of 0.1 to 0.8 kg for use as a binder; nicotinic acid in the amount of 0.25 to 0.9 kg for use as a seed germination stimulator; Unum in the amount of 0.005 kg for use as a fertilizer; Vitavax in the amount of 0.5 to 2.0 kg for use as a fungicide; Titus in the amount of 0.05 to 0.3 kg for use as a herbicide, and 25 to 30 liters of water for use as a solvent.

8. The biologically active nanochip according to claim 1 for treating tomato seeds, comprising the following components in the amounts per 1 ton of seeds: diatomite in the amount of 10 to 25 kg for use as a carrier; chitosan in the amount of 0.10 to 0.20 kg for use as a fungicide and a plant-growth regulator; glutamic acid in the amount of 0.10 to 0.25 kg; succinic acid in the amount of 0.50 to 0.90 kg for use as a plant-growth regulator; biological humus in the amount of 0.10 to 0.20 kg for use as a fertilizer; Akrobat® in the amount of 0.0075 to 0.03 kg for use as a fungicide; Karate in the amount of 0.0005 to 0.005 kg for use as a fungicide, and 10 to 20 liters of water for use as a solvent.

9. The biologically active nanochips according to claim 1, wherein said biologically active nanochips have dimensions ranging from several microns to 2 mm, and wherein pores of the carriers have nano dimensions.

10. The biologically active nanochips according to claim 2, wherein said biologically active nanochips have dimensions ranging from several microns to 2 mm, and wherein pores of the carriers have nano dimensions.

11. Biologically active nanochips for treating seeds of agricultural plants in order to improve seed germination conditions and development of plants and for protecting plants from anticipated and averaged adverse conditions, said biologically active nanochips comprising at least one of each of the following components used in the amounts shown in percentage contents:
   biologically active substance: $1 \cdot 10^{-10}$% to 100%
   carrier for physiologically active substance(s): $1 \cdot 10^{-2}$% to 10%
   plant-growth regulator: $1 \cdot 10^{-10}$% to 1%
   phytosanitary agent: $1 \cdot 10^{-5}$% to 10%
   nutrient element: $1 \cdot 10^{-2}$% to 90%
   solvent: the balance
wherein said at least one carrier and said at least one biologically active component being indispensable components of the biologically active nanochips and at least one plant-growth regulator, at least one phytosanitary agent, at least one nutrient element, and at least one solvent being selected and included with reference to said anticipated and averaged adverse conditions, said at least one carrier having pores capable of accommodating biologically active nanochips or surfaces capable of holding biologically active nanochips.

12. The biologically active nanochips according to claim 11, wherein said biologically active nanochips have dimensions ranging from several microns to 2 mm, and wherein pores of the carriers have nano dimensions.

13. The biologically active nanochips according to claim 11, wherein phytosanitary agents are selected from a group consisting of insectofungicides, bactericides, herbicides, nematocides, acaricides, antiviral preparations and substances that induce protective functions in plants, immunomodulators, elicitors, and desiccants.

14. The biologically active nanochips according to claim 11, wherein said biologically active nanochips have dimensions ranging from several microns to 2 mm, and wherein pores of the carriers have nano dimensions.

15. A method for treating seeds of agricultural plants prior to sowing with biologically active nanochips in order to improve seed germination conditions and development of plants and for protecting plants from anticipated and averaged adverse conditions, said biologically active nanochips comprising at least one of each of the following components:
   carrier for carrying physiologically active components; and
   biologically active component carried by said carrier and selected from the group comprising at least one of each of the following:
   binder;
   nanochip stabilizer;
   herbicide;
   plant-growth regulator;
   seed-germination stimulator;
   fungicide;
   bactericide;
   fertilizer;
   nutritive component; and
   one solvent,
   wherein at least one carrier and at least one biologically active component being indispensable components of the biologically active nanochips and the other biologically active components being selected and included with reference to said anticipated and averaged adverse conditions, said at least one carrier having pores capable of accommodating the biologically active nanochips or surfaces capable of holding the biologically active nanochip, said method comprising the following steps:
   determining anticipated and average adverse conditions in the area where agricultural plants are to be grown;
   selecting biologically active components from the above group that most optimally match said anticipated and averaged adverse conditions;
   presorting the seeds to be treated by passing the seeds through sieves having cell diameters corresponding to seed dimensions;
   coating the seeds with a dosed amount of a solution that contains the biologically active nanochips;
   drying the treated seeds; and
   storing the treated seeds until sowing.

16. The method of claim 15, further comprising the following steps:
   providing an apparatus for presowing treatment of seeds comprising an accumulation hopper, a rotary pelletizer drum, a dosing device, a feed screw, and a receiving hopper;
   loading the seeds into the accumulating hopper;
   periodically unloading the seeds under gravity from the accumulating hopper onto the rotary pelletizer drum;
   preparing a finely dispersed homogeneous colloidal solution that contains the biologically active nanochips;
   spraying the surfaces of the biologically active nanochips in the rotary pelletizer drum while the seeds are tumbled and mixed in the rotary pelletizer drum;
   unloading the treated seeds into the feed screw; and
   drying the seeds during transportation in said feed screw.

17. The method of claim 16, wherein the treated seeds are dried in a flow of air heated to a temperature of 20 to 30° C.

18. The method of claim 15, wherein said at least one carrier having pores capable of accommodating the biologically active nanochips or surfaces capable of holding the biologically active nanochips.

19. The method of claim 15, wherein said at least one carrier having pores capable of accommodating the biologically active nanochips or surfaces capable of holding the biologically active nanochips.

20. The method of claim 15, wherein said biologically active nanochips have dimensions ranging from several microns to 2 mm, and wherein pores of the carriers have nano dimensions.

* * * * *